(12) United States Patent
Zeitler et al.

(10) Patent No.: US 9,683,934 B2
(45) Date of Patent: Jun. 20, 2017

(54) TERAHERTZ SPECTROSCOPY FOR PREDICTING STABILITY OF AMORPHOUS DRUGS

(71) Applicant: Cambridge Enterprise Limited, Cambridge (GB)

(72) Inventors: Jochen Axel Zeitler, Cambridge (GB); Juraj Sibik, Basel (CH)

(73) Assignee: Cambridge Enterprise Limited, Cambridge, MA (US)

( * ) Notice: Subject to any disclaimer, the term of this patent is extended or adjusted under 35 U.S.C. 154(b) by 0 days.

(21) Appl. No.: 15/030,348

(22) PCT Filed: Oct. 17, 2014

(86) PCT No.: PCT/GB2014/053123
§ 371 (c)(1),
(2) Date: Apr. 18, 2016

(87) PCT Pub. No.: WO2015/056030
PCT Pub. Date: Apr. 23, 2015

(65) Prior Publication Data
US 2016/0238523 A1    Aug. 18, 2016

(30) Foreign Application Priority Data

Oct. 18, 2013  (GB) .................................. 1318493.2
Apr. 1, 2014   (GB) .................................. 1405843.2

(51) Int. Cl.
*G01J 5/02*        (2006.01)
*G01N 21/3581*     (2014.01)
(Continued)

(52) U.S. Cl.
CPC ..... *G01N 21/3581* (2013.01); *G01N 21/3586* (2013.01); *G01N 33/15* (2013.01); *G01N 2201/06113* (2013.01)

(58) Field of Classification Search
CPC .................................................. G01N 21/3586
See application file for complete search history.

(56) References Cited

PUBLICATIONS

Naftaly et al., "Terahertz time-domain spectroscopy for material characterization," 2007, Proceedings of the IEEE, vol. 95, No. 8, pp. 1658-1665.*

(Continued)

*Primary Examiner* — Kiho Kim
(74) *Attorney, Agent, or Firm* — Blank Rome LLP

(57) ABSTRACT

A method for characterizing an amorphous material involves an evaluation of a rate of change with temperature of an interaction of the amorphous material with electromagnetic (EM) radiation. The interaction is at an energy of between $6.6 \times 10^{-24}$ J and $6.6 \times 10^{-21}$ J, which corresponds to EM radiation in the terahertz band, between 10 GHz and 10 THz. The rate of change of the interaction is evaluated in a temperature range below a glass transition temperature ($T_g$) of the amorphous material. The rate of change can then be compared with a predetermined value in order to characterize the amorphorous material. An apparatus is provided to carry out the method, and the method can produce amorphous materials having desired properties, such as stability against crystallization.

20 Claims, 9 Drawing Sheets

(51) Int. Cl.
    *G01N 21/3586*    (2014.01)
    *G01N 33/15*      (2006.01)

(56) References Cited

PUBLICATIONS

J. Sibik et al., "Glassy Dynamics of Sorbitol Solutions at Terahertz Frequencies." Phys. Chem. Chem. Phys., vol. 15, pp. 11931-11942, 2013.

J. Sibik et al., "Terahertz Spectroscopy of Hydrogen-Bonded Glass-Forming Liquids." 2013 38th International Conference on Infrared, Millimeter, and Terahertz Waves, Sep. 1, 2013, pp. 1-3.

J. Axel Zeitler et al., "Relaxation and Crystallization of Amorphous Carbamazepine Studied by Terahertz Pulsed Spectroscopy." Journal of Pharmaceutical Sciences, vol. 96, No. 10, pp. 2703-2709, Oct. 2007.

M. Otsuka et al.,"Characterization of Poly-Amorphous Indomethacin by Terahertz Spectroscopy." J. Infrared Milli. Terahz. Waves, vol. 33, pp. 953-962, 2012.

\* cited by examiner

TERAHERTZ SPECTROSCOPY FOR PREDICTING STABILITY OF AMORPHOUS DRUGS

FIELD OF INVENTION

The invention relates to a method and an apparatus for characterising amorphous materials, and in particular to a method and an apparatus for assessing the stability of amorphous materials, for example during storage.

BACKGROUND OF INVENTION

Over the past decades, research and development activities in the pharmaceutical industry have lead to the discovery of thousands of new molecules and chemical structure motifs that have a strong potential to be used in the treatment of human diseases; yet only a small proportion of these lead candidates have made it to the market. Increasingly, low solubility and complex polymorphism of lead molecules limit the suitability of these molecules, and a number of products based on such molecules are failing just before introduction to the market. At the same time, the number of recalls of products on the market due to problems originating from their physico-chemical properties is on the rise.

One very promising approach to increase the solubility of a pharmaceutical is to formulate the molecules of the pharmaceutical into an amorphous phase, which is higher in energy than the crystalline state and hence intrinsically tends to exhibit higher solubility. It is fairly straightforward to make drug molecules amorphous and an associated increase in bioavailability for an amorphous drug compared to its crystalline counterparts has been demonstrated. However, the amorphous state is thermodynamically unstable and currently it is impossible to predict whether or not an amorphous drug will be stable over the shelf life of the drug product. This problem means that the commercial application of the strategy of making drug molecules amorphous is currently extremely limited.

Similar problems arise in fields other than pharmaceuticals, such as in relation to foods, cosmetics, consumer chemicals, paints and the like, in which performance enhancements may be gained by using molecules in an amorphous form but in which the stability of the amorphous form cannot be predicted.

SUMMARY OF INVENTION

The invention provides a method, an apparatus and an amorphous material as defined in the appended independent claims, to which reference should now be made. Preferred or advantageous features of the invention are set out in dependent subclaims.

References to amorphous materials in the following description should be taken to include partially amorphous materials, and material compositions such as mixtures in which only one or some of the components of the material are amorphous, as the skilled person would appreciate.

The invention in its various aspects may thus advantageously provide a method and apparatus for the use or measurement of the terahertz dynamics of an amorphous material to correlate with or predict the stability, or resistance to crystallisation, or stabilising effect, or rigidity, of the amorphous material.

In a first aspect, the invention may therefore advantageously provide a method for characterising an amorphous material, comprising the steps of: evaluating a rate of change with temperature of an interaction of the amorphous material with electromagnetic (EM) radiation, the interaction being at an energy corresponding to EM radiation of frequency between 10 GHz and 10 THz, in a range of temperatures below a glass transition temperature, $T_g$, of the amorphous material; and comparing the rate of change with a predetermined value. In a preferred embodiment, the frequency range may have a lower limit of 100 GHz and/or an upper limit of 3 THz.

The interaction is at an energy corresponding to an EM frequency in this range so as to measure dynamics of the amorphous material in this energy, or EM frequency, range (such as terahertz dynamics). In other words the interaction for the amorphous material may be at an energy of between $(6.6 \times 10^{-24}$ J and $6.6 \times 10^{-21}$ J), or in a preferred embodiment between $6.6 \times 10^{-23}$ J and $2.0 \times 10^{-21}$ J, these energies corresponding to the frequencies of EM radiation mentioned above.

Thus, for example, the interaction may comprise, or relate to, a loss of EM radiation in the specified frequency range on passing through the amorphous material.

Alternatively, the interaction may comprise, or relate to, an intensity of radiation scattered from the amorphous material, for example deriving from EM radiation or other energy incident on the amorphous material. Such scattered EM radiation may correspond to, or be derived from, a dynamic or characteristic of the amorphous material in the desired 10 GHz to 10 THz frequency range. The scattered EM radiation may thus itself have a frequency between 10 GHz and 10 THz, or it may derive from an energy shift or frequency shift in the amorphous material corresponding to this frequency range. Thus, for example, a frequency shift in the range 10 GHz to 10 THz, or in the preferred range 100 GHz to 3 THz, or other preferred range described herein, may be a shift of frequency between scattered EM radiation and incident (exciting) EM radiation after interacting with the amorphous material.

In a further alternative, the interaction at an energy corresponding to an EM frequency in the desired range may arise from other interactions such as fluorescence, as may be measured, for example, by fluorescence spectroscopy. A suitable technique may be time-resolved fluorescence spectroscopy such as time-resolved fluorescent Stokes shift spectroscopy.

In preferred embodiments, the interaction may therefore be measured by measurement of EM radiation loss or absorption, or by a frequency-shift technique using scattering such as Raman, VIS (visible) light or neutron spectroscopy, or using fluorescence, such as time-resolved fluorescent Stokes shift spectroscopy.

Other methods may also be used to characterise or evaluate the interaction of the amorphous material in the desired energy range, such as Fourier Transform Infra Red spectroscopy (FTIR), Infra Red spectroscopy (IR), near-infrared spectroscopy (near-IR), or Nuclear Magnetic Resonance spectroscopy (NMR).

The rate of change may advantageously be evaluated by measuring EM radiation within a temperature range. The measurement range may fall both above and below $T_g$, or may fall below $T_g$, or may fall below 1.2 $T_g$. The rate of change of the interaction of the amorphous material with EM radiation (such as the rate of change of EM loss or the rate of change of the intensity of scattered radiation or other suitable measurement, including the methods described herein) with temperature in a desired temperature range below $T_g$ may be evaluated using measurements made outside the desired temperature range, such as above $T_g$, or the evaluation of the rate of change of the interaction with temperature in the desired temperature range may be made more accurate by including measurements made outside the desired temperature range.

In a first embodiment of the invention the desired temperature range for evaluation of the rate of change of loss of EM radiation may have a lower limit falling between 0.4, 0.5 or 0.55 $T_g$, and 0.8, 0.7 or 0.66 $T_g$. A particularly preferred lower limit may be about 0.6 $T_g$. In an embodiment of the invention, measurements may be made at a plurality of temperatures within the range.

A further aspect of the invention may advantageously involve the steps of; evaluating a first value of the rate of change within a temperature range between $T_g$ and a transition temperature below $T_g$; evaluating a second value of the rate of change within a temperature range below the transition temperature; and evaluating a difference between the first and second rates of change. The difference may then be compared with a predetermined difference value in order to characterise the amorphous material. Preferably, the lower the value of the difference, the greater the stability of the amorphous material against crystallisation.

In a preferred embodiment, the second value of the rate of change, below the transition temperature, may be used as the predetermined value, or threshold value, to which the first value of the rate of change may be compared.

The transition temperature may, for example, be above a lower limit of 0.4, 0.5 or 0.55 $T_g$, and/or below an upper limit of 0.8, 0.7 or 0.65 $T_g$. The transition temperature is preferably about 0.6 $T_g$.

In the aspects of the invention described above, the interaction may advantageously be measured, or in respect of energies corresponding to, at a frequency or frequencies above 10 GHz, 100 GHz, 0.5 THz or 0.75 THz, and/or below 10 THz, 3 THz, 2 THz or 1.5 THz. A preferred frequency is about 1 THz.

To provide the most effective or accurate output, the interaction may be measured at more than one frequency (or corresponding energy) within a range of frequencies (such as within a range of frequencies described herein). The rate of change of the interaction with temperature may then advantageously be evaluated for the measured EM frequency providing the interaction data with the highest signal-to-noise ratio.

The inventors' understanding is that the method and apparatus of the invention is sensitive to motion, or vibration, of molecules in amorphous materials. In particular, the method may be sensitive to the vibration of hydrogen-bonded molecules. Thus, in a preferred embodiment the amorphous material comprises a hydrogen-bonded amorphous material. Thus, for example, the amorphous material may comprise a polymeric material.

In view of this understanding the efficacy of the methods for characterising or evaluating the interaction of the amorphous material may be better understood. Techniques such as Terahertz spectroscopy may be used to excite directly two or more hydrogen-bonded molecules. This is because the energy of vibration of the hydrogen bond itself may be within the specified energy range of the interaction of the amorphous material.

Alternative techniques may be responsive to the strength, or the energy of the hydrogen bond without directly measuring that parameter. For example in a hydrogen-bonded molecule a group such as an —OH or —NH or —H group may be bonded to a carbon atom in the molecule and may be hydrogen-bonded to an adjacent molecule. In that case the energy or vibration of the OH or NH or CH bond may be affected by the hydrogen bond and so measurement of the energy or vibration of the OH or NH or CH bond may allow characterisation or evaluation of the hydrogen bond. This may be achieved, for example, by using FTIR to measure stretching or other vibrational modes of the OH or NH or CH bond.

In its various aspects, the invention may advantageously allow a step of using the characterisation of the amorphous material to assess or predict the resistance to crystallisation of the amorphous material, for example under predetermined conditions, or during storage of the material, even over a long time period before the amorphous material (such as a pharmaceutical or other useful material) is used.

In aspects of the invention, the interaction of the amorphous material with EM radiation may be expressed in various ways, including in terms of an absorption coefficient of the amorphous material, a dielectric loss value for the amorphous material, an extinction coefficient for the amorphous material, an amplitude of transmittance, an amplitude of reflectance, an amplitude of time-domain peak, or absorbance, an intensity or amplitude of scattered radiation, or any combination of these.

The invention may thus advantageously provide a powerful new method to characterise or predict the stability of amorphous materials, such as drug molecules in amorphous form, based on their dielectric properties at terahertz frequencies, for example as measured by terahertz time-domain spectroscopy. In addition, the invention may advantageously provide a method and apparatus for enabling the development of methods for stabilisation of amorphous materials. For example, if an amorphous material shows inadequate stability for a particular purpose, it may be possible to increase or enhance its stability by various techniques, such as mixing it with another material such as a polymer. By using a method or apparatus embodying the invention to characterise the stability of such new formulations, formulations with improved stability may be developed. Similarly, a method or apparatus embodying the invention may thus be used to characterise the stabilising effect of components in formulations, such as pharmaceutical formulations, in which an amorphous component (such as a sugar-glass matrix) is used to stabilise another component (such as a freeze-dried protein or nucleic acid).

A Biopharmaceuticals Classification System (BCS) is used in the pharmaceutical industry to assess properties of pharmaceuticals. Solubility plays an essential role in drug delivery, since the maximum rate of passive drug transport across a biological membrane, the main pathway for drug absorption, is the product of permeability and solubility. Aqueous solubility is a crucial molecular property for successful drug development as it is a key factor governing drug access to biological membranes.

The number of poorly water-soluble drug candidates has recently risen sharply, particularly with recent progress in combinatorial chemistry and high-throughput screening. Development of oral formulations for such compounds can put forward significant challenges at all stages of drug development. Insufficient bioavailability of these compounds due to their low solubility may result in delays in development or cause them to be dropped from the pipeline.

The BCS is used in drug development to split pharmaceutical compounds into four classes based on their bioavailability:

Class I—high permeability, high solubility. Those compounds are well absorbed and their absorption rate is usually higher than excretion.

Class II—high permeability, low solubility. The bioavailability of those products is limited by their solvation rate. A correlation between the in vivo bioavailability and the in vitro solvation can be found.

Class III—low permeability, high solubility. The absorption is limited by the permeation rate but the drug is solvated very fast. If the formulation does not change the permeability or gastro-intestinal duration time then class I criteria can be applied.

Class IV—low permeability, low solubility. Those compounds have a poor bioavailability. Usually they are not well absorbed over the intestinal mucosa and a high variability is expected.

As can be seen in FIG. 1, 30% of currently-marketed drugs fall into BCS Class II. The figure is much more dramatic for the drugs in development where approximately 70% of the drugs suffer from poor solubility.

Several strategies may be utilized in order to improve Active Pharmaceutical Ingredients' (APIs) solubility. On a molecular level this includes usage of prodrugs (a prodrug is a drug administered to the body as a precursor to the intended drug) or a formation of salts. On the particulate level the particle size can be mechanically reduced in order increase the surface area and thereby improve the solubility. Common methods for particle size reduction are spray-drying or milling techniques.

A different way to improve a drug's solubility is to prepare it into an amorphous solid form (lacking a long-range molecular order, e.g. glass) instead of the commonly-used crystalline solid form (where molecules are arranged in a periodic cell). The amorphous materials generally have better solubility properties. On the other hand it is very difficult to formulate an amorphous drug into a sufficiently stable form as regulatory requirements dictate that a drug product must not degrade chemically or mechanically over at least 1-2 years after production. These requirements are also different for different types of drug.

There are two main difficulties related to the determination of stability of amorphous materials. First is a lack of understanding of amorphous matter. For a long time scientists have suggested that the crucial parameter is the glass-transition temperature, $T_g$, i.e. the temperature where a liquid solidifies into an amorphous form if the necessary criteria are met in order to avoid crystallization of the liquid (such as imposition of sufficiently high cooling rate etc.). This seems intuitively correct as it is at the glass-transition temperature that the molecules become spatially arrested and their mobility is significantly reduced, preventing a crystal seed from diffusing and growing. During the current, conventional formulation of small-molecule amorphous drugs the focus is therefore commonly given to shifting $T_g$ to high values by adding extra components to the formulation (such as polymers). The aim is to achieve a $T_g$ above room temperature (or more precisely, above the storage temperature of the drug). This approach is based purely on the temperature difference between storage temperature and $T_g$. However this empirical method does not work reliably and very often amorphous drugs crystallize even when stored below $T_g$.

The inventors' recent investigations give a much deeper insight and a new solution to the problem of characterising or predicting the resistance to crystallisation of amorphous materials. They have found that even at temperatures below $T_g$ a part of the molecular mobility is preserved, which may allow an onset of crystallization, and they have developed a method and apparatus for assessing the amount of that molecular mobility.

The inventors have found that this is a property which can be used to predict or characterise amorphous material stability, and the invention may advantageously provide a method or apparatus for the measurement of this molecular mobility of amorphous materials, such as amorphous drugs or pharmaceuticals, below $T_g$.

The inventors have found that information on the molecular mobility of amorphous materials can be extracted from measurement of interactions with the amorphous material at terahertz frequencies (10 GHz to 10 THz) or involving energy shifts or transitions in the material corresponding to energies of terahertz EM radiation ($6.6 \times 10^{-24}$ J to $6.6 \times 10^{-21}$ J), such as the dielectric losses of a sample of the material at terahertz frequencies ($\sim 10^{12}$ Hz), as described herein. FIG. 2 illustrates (without limiting the generality of the invention) the inventors' current understanding that the overall measured absorption of amorphous solids at terahertz frequencies in general originates from factors including (i) the primary ($\alpha$) dielectric relaxation, (ii) the slow secondary ($\beta$) dielectric relaxation, (iii) fast secondary dielectric relaxation, (iv) vibrational density of states (VDOS) and (v) ionic conductivity if ions are present (e.g. in salts). Point (v) is not considered here as the materials in our current focus do not contain ions.

The inventors' realisation leading to the invention is that the process responsible for sub-$T_g$ molecular mobility is the secondary dielectric relaxation. Therefore by extracting the contribution of the secondary dielectric relaxation to the terahertz absorption spectrum of a material, it may be possible to determine the level of molecular mobility in the material below $T_g$. The VDOS peak is clearly observable at very low temperatures (below 0.6 $T_g$) and is expected to be independent of temperature. The primary dielectric relaxation changes dramatically with temperature, but contributes to losses at terahertz frequencies only at temperatures above $T_g$. Therefore any temperature-dependent part of absorption at temperatures below $T_g$ is related to the slow and/or fast secondary dielectric relaxation process. Its contribution commonly vanishes from terahertz spectra at around 0.6 $T_g$, while no such behaviour is observed for the fast secondary dielectric relaxation.

This has two implications which underpin aspects or preferred features of the method and apparatus of the present invention:

1) That the linear thermal coefficient B of absorption coefficient $\alpha$ from equation $\alpha'' = A + B \cdot T/T_g$, where T is temperature, provides a good metric for characterization of remaining molecular mobility between a transition temperature of about 0.6 $T_g$ and the glass transition temperature 1.0 $T_g$, or a slightly higher temperature up to about 1.2 $T_g$, and thus the stability of an amorphous material against crystallization. As alternatives to the absorption coefficient, other parameters such as dielectric losses $\in''$, absorbance, kappa or terahertz electric field may be used; these are all related parameters as the skilled person would be aware. Corresponding measurements using scattering techniques such as Raman spectroscopy or measurement using other techniques such as FTIR may similarly be effective, as described herein.

$\alpha = A/d$, where a is the absorption coefficient, A is absorbance and d is thickness of a sample; $\kappa = \alpha c/(4\pi\nu)$, where c is speed of light and n and $\kappa$ (kappa) are the real and imaginary parts of the complex refractive index, respectively; $\in'' = 2n\kappa$, where $\in''$ are the dielectric losses (imaginary part of the complex dielectric function).

2) That for temperatures below the transition temperature of about 0.6 $T_g$ the molecular mobility (and thus the glass, or amorphous-material, instability) caused by the secondary dielectric relaxation substantially vanishes. It is the inventors' understanding that the slow secondary relaxation is the main source of molecular mobility responsible for crystallisation below $T_g$.

The invention in its various aspects thus involves the use or measurement of the terahertz dynamics of an amorphous material to correlate with the stability of the amorphous phase of the material. The measurement of the terahertz dynamics may allow observation of the molecular mobility at terahertz frequencies.

In a preferred embodiment of the invention, such measurements may be made using a terahertz time-domain spectroscopy (THz-TDS) method and apparatus but the method is, in more general terms, not limited to this technology. It may advantageously include a method and apparatus generally applicable to the analysis of measurement data from any other technique that is currently available or will be available in the future to measure the dielectric properties of materials at these frequencies (energies). For example, synchrotron or free-electron lasers may be usable to measure dielectric losses at terahertz frequencies, as well as interferometric techniques of dielectric spectroscopy. Scattering techniques such as Raman spectroscopy may also be used.

The invention may thus, in particular, provide a game-changing tool for pharmaceutical and biotechnology companies allowing them systematically to evaluate and develop BCS Class II drugs into suitable physical forms, such as oral solid-dosage forms. Based on the measurements from embodiments of the invention, it may be possible to predict which drug molecules or formulations can be successfully developed into tablets that will maintain amorphous stability throughout the shelf life of a desired product. This may advantageously allow the development of a significant proportion of candidate drug molecules into drug products that would otherwise drop out of the development pipeline due to solubility problems. The technology has a huge potential economic impact. The size of the total pharmaceutical market is currently approximately US $850 bn with expected growth to over US $1100 bn by 2014. Traditional small-molecular drugs account for 70% (US $600 bn) and biopharmaceuticals 15% (US $100 bn) of the market. Out of the small-molecular drugs, currently about 30% fall into BCS Class II (US $180 bn). The number of drugs that are rejected during development due to poor solubility is even more significant: approximately 40% of all lead compounds do not reach the market due to their poor solubility.

The method may advantageously be applicable to all amorphous materials, such as amorphous drug products, no matter how they are prepared (for example by melt extrusion, melt quenching, milling, spray drying etc.). The method of the invention is fundamentally different compared to any existing technology.

The method and apparatus of the invention may additionally be applicable to aid the formulation development of biopharmaceuticals for applications such as protein formulation stabilisation of freeze-dried proteins or peptides.

However, it is important to note that this method may provide a substantially universal approach to assess amorphous material stability and the commercial applications of this technology reach far beyond the pharmaceutical industry with a range of applications in the food industry (freeze-dried products, amorphous confectionery, etc.), the cosmetic industry, paint industry and others.

A further aspect of the invention provides an apparatus for characterising amorphous materials. This aspect of the invention may thus advantageously provide an apparatus for characterising an amorphous material, comprising:

a spectrometer for measuring an interaction between the amorphous material and electromagnetic (EM) radiation at an energy corresponding to EM radiation of frequency between 100 GHz and 3 THz ($6.6 \times 10^{-24}$ J to $6.6 \times 10^{-21}$ J), at each of a plurality of temperatures, or over a range of temperatures, less than or equal to a glass transition temperature, $T_g$, of the amorphous material; and a processor for evaluating a rate of change of the interaction with temperature and for comparing the rate of change with a predetermined value.

The apparatus may thus advantageously be programmed for, or otherwise capable of, measuring the interaction and evaluating the rate of change within a temperature range between $T_g$ and a lower temperature and, preferably, of comparing the result with a predetermined value. The apparatus may also, for example, be capable of measuring the interaction and evaluating a first value of the rate of change within a temperature range between $T_g$ and a transition temperature below $T_g$, measuring the interaction and evaluating a second value of the rate of change within a temperature range below the transition temperature, evaluating a difference between the first and second rates of change, and comparing the difference with a predetermined difference value.

In a still further aspect, the invention may advantageously provide an amorphous material produced using a characterisation method or apparatus embodying the invention.

SPECIFIC EMBODIMENTS OF THE INVENTION

Specific embodiments of the invention will now be described by way of example, with reference to the accompanying drawings, in which.

Figure 4:
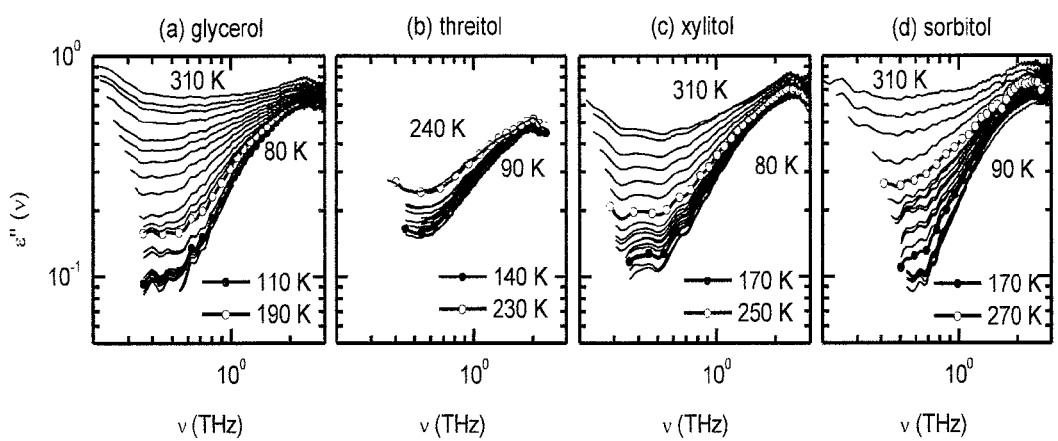
Figure 5:
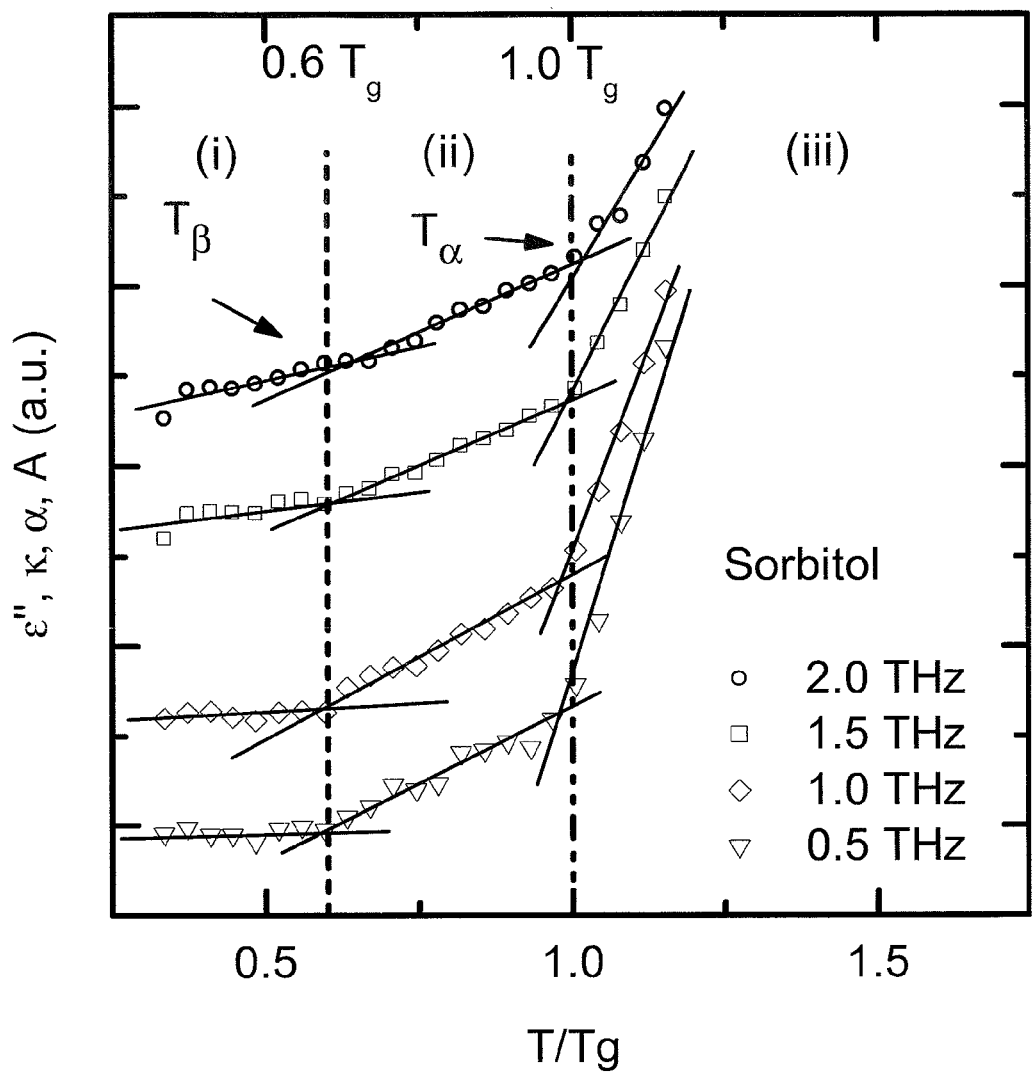
Figure 6:
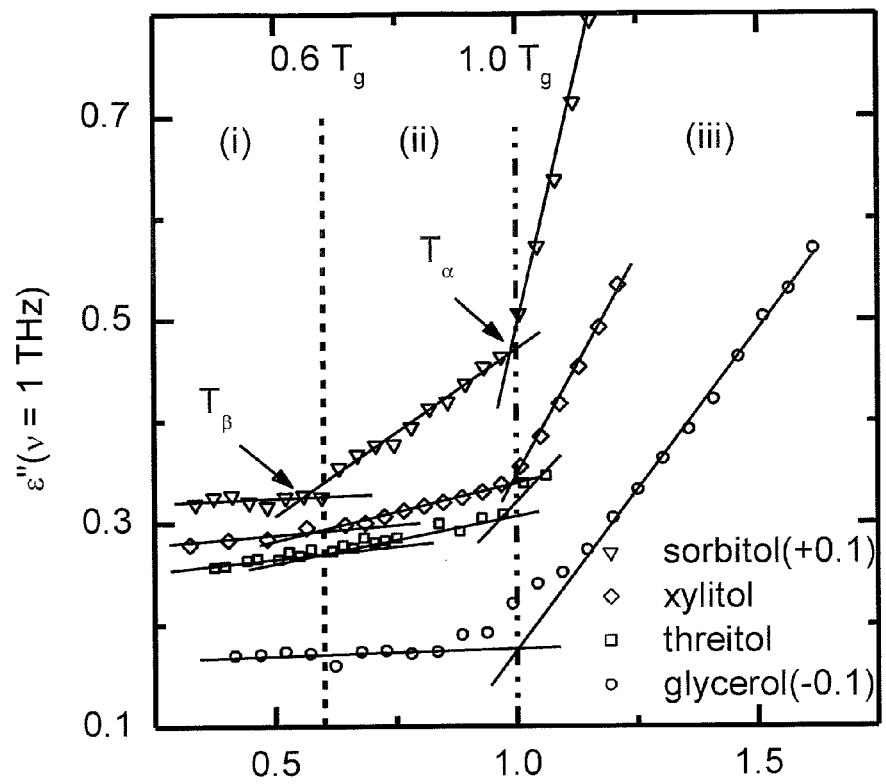
Figure 10:
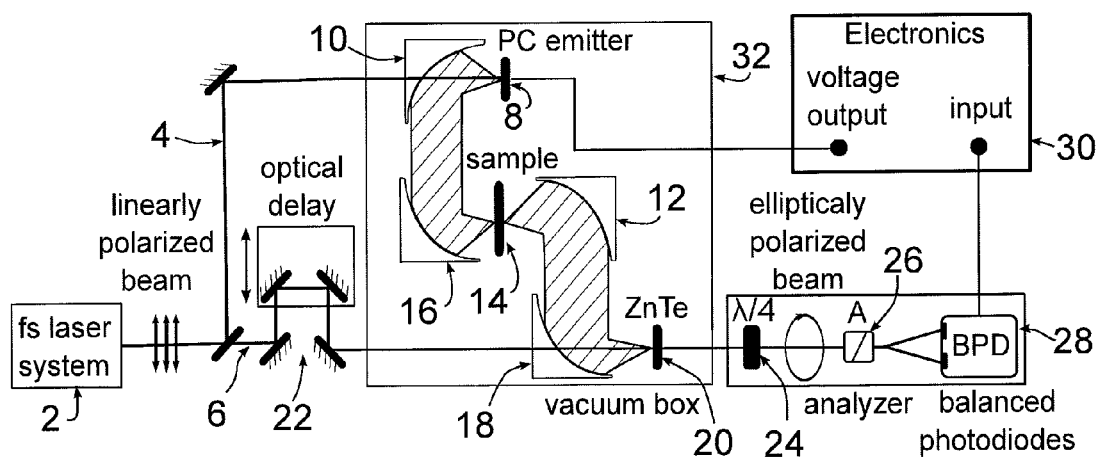
Figure 7:
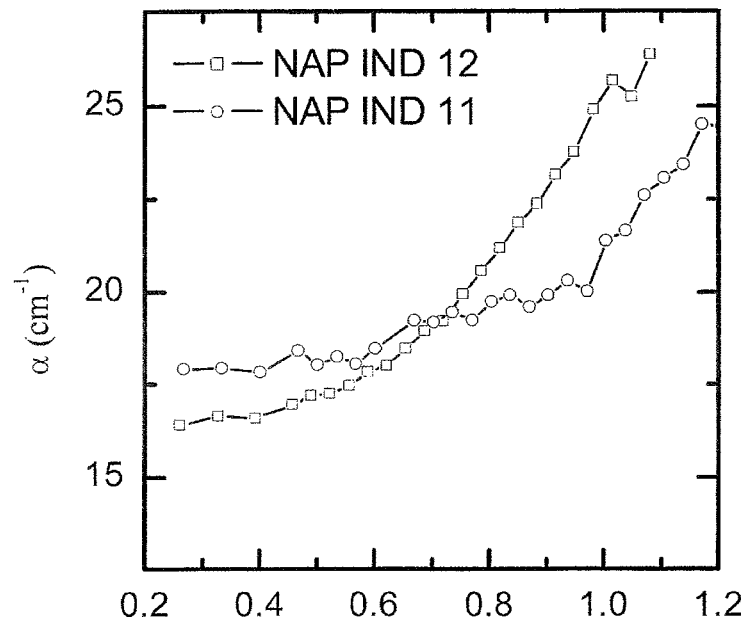
Figure 8:
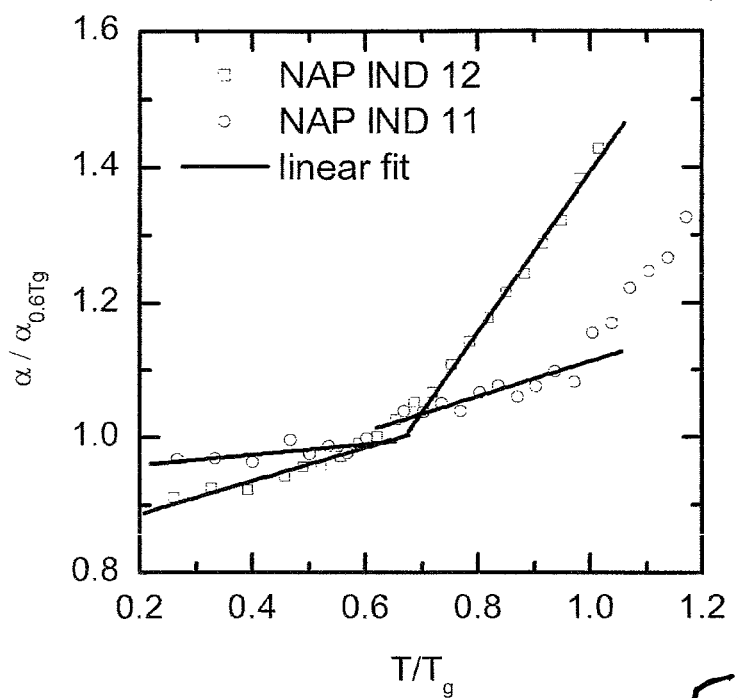
Figure 9:
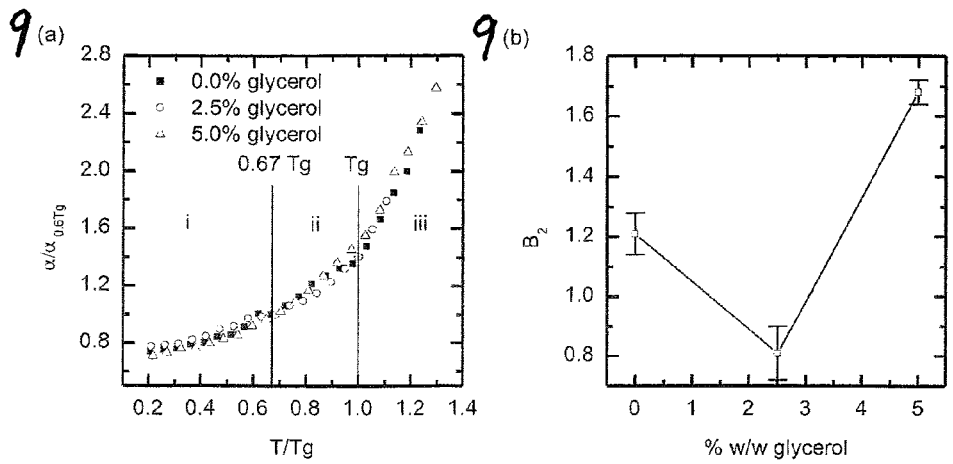
Figure 11:
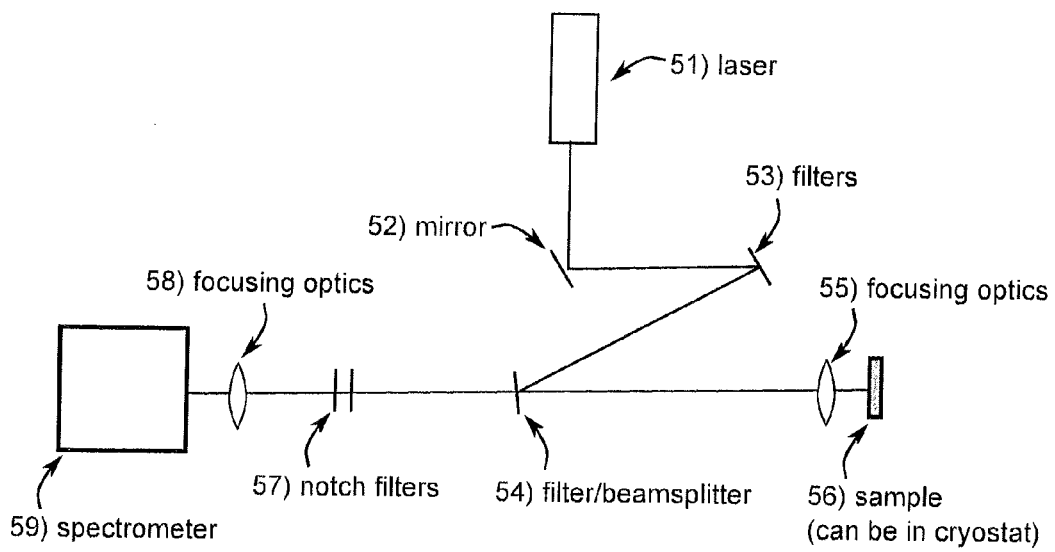
Figure 12:
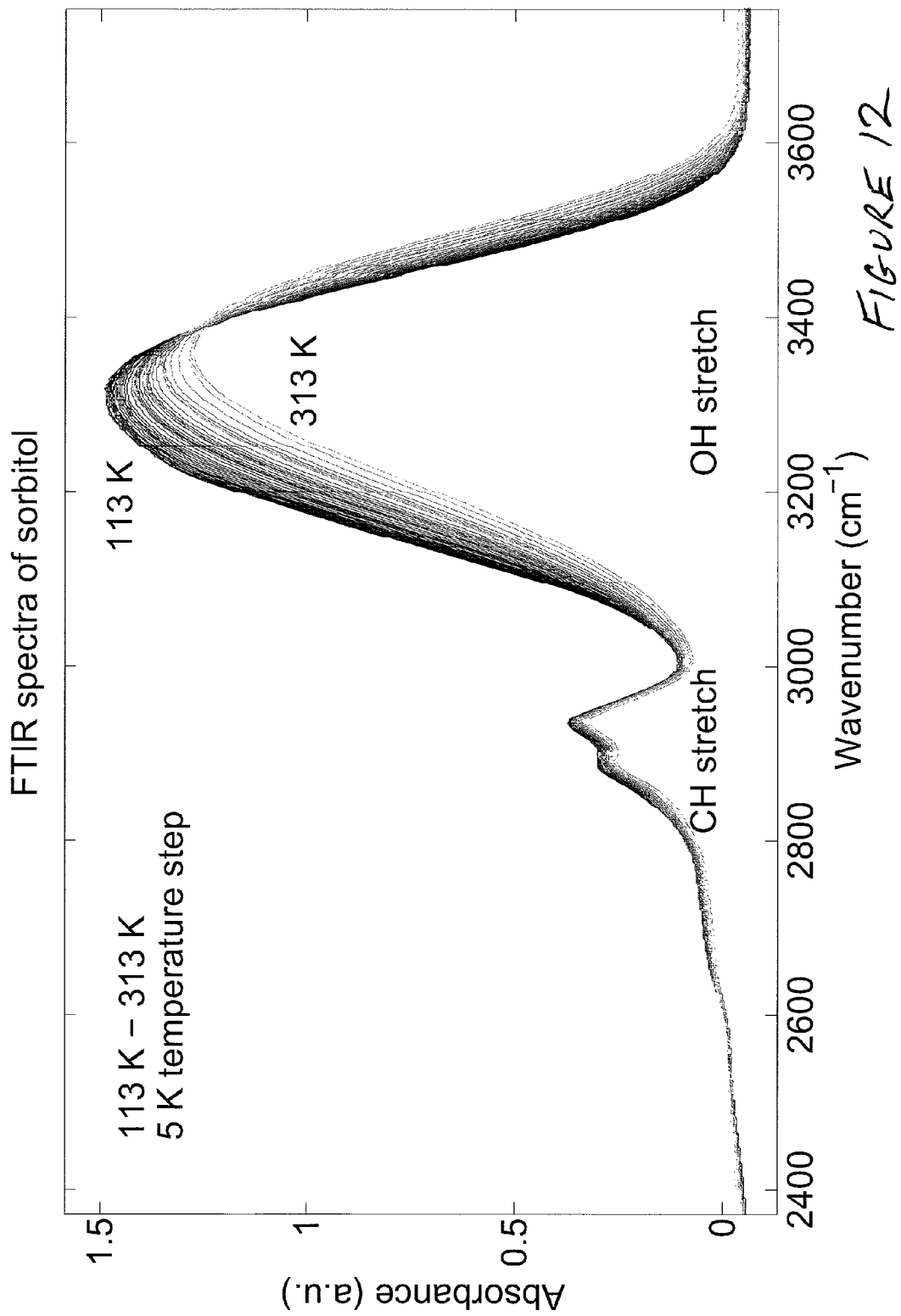
Figure 13:
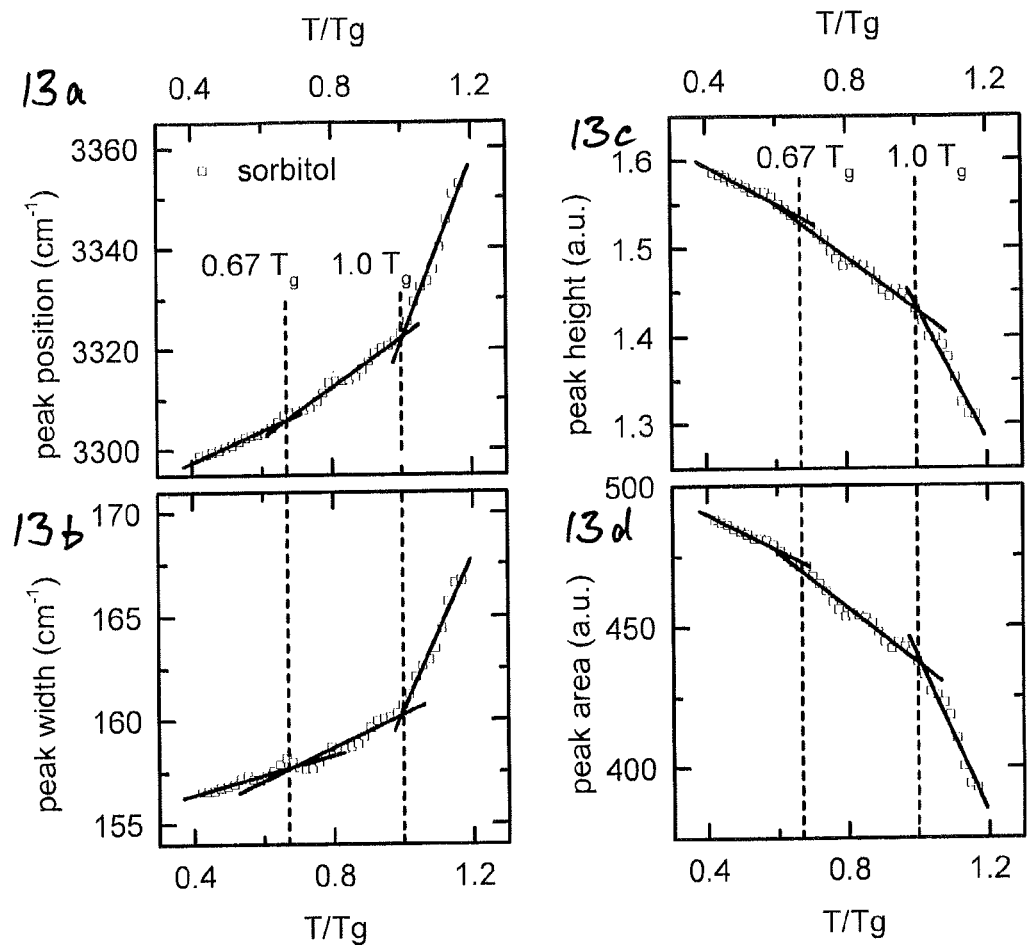

FIG. 4 is a plot of the dielectric losses $\in''(v)$ of: (a) glycerol; (b) threitol; (c) xylitol; and (d) sorbitol, at terahertz frequencies in the temperature range 80-310 K with 10 K temperature increments. The filled and empty circles highlight the losses in the proximity of 0.6 $T_g$ and $T_g$, respectively. The sample of threitol recrystallised above 250 K and only data below this temperature are shown in this figure;

FIG. 5 is a plot for sorbitol of the dielectric losses $\in''$ ($T/T_g$) at four different terahertz frequencies. The solid lines represent linear fits to the data in regions (i), (ii) and (iii), as explained in the text below. The dashed vertical lines highlight the temperatures 0.6 $T_g$ and $T_g$, respectively. $T_\beta$ and $T_\alpha$ represent the crossover points of the linear fits from region (i) to region (ii), and from region (ii) to region (iii), respectively;

FIG. 6 is a plot for four polyalcohols of the dielectric losses $\in''$ ($T/T_g$) at a frequency $v=1$ THz. The solid lines represent linear fits to the data in regions (i), (ii) and (iii), as explained in the text below. The dashed vertical lines highlight the temperatures 0.6 $T_g$ and $T_g$, respectively. $T_\beta$ and $T_\alpha$ represent the crossover points of the linear fits from region (i) to region (ii), and from region (ii) to region (iii), respectively. The dielectric-loss data for sorbitol and glycerol are offset vertically in the positive and negative directions by 0.1, respectively, for clarity;

FIG. 7 is a plot showing the absorption of naproxen:indomethacin in two molar mixtures, 1:2 (squares) and 1:1 circles, at 1 THz plotted against the rescaled temperature $T/T_g$;

FIG. 8 is a plot of the rescaled absorption coefficient $\alpha/\alpha_{0.6Tg}$ of the naproxen:indomethacin molar mixtures of FIG. 7 against the rescaled temperature $T/T_g$; the black lines in the plot show linear fits of the data $\alpha/\alpha_{0.6Tg}=C+DT/T_g$ in a given thermal region;

FIG. 9 shows plots of terahertz absorption coefficient of amorphous trehalose/glycerol mixtures; 9(a) shows temperature dependence of the mixtures reduced absorption spectra $\alpha/\alpha_{0.6Tg}$ on reduced temperature $T/T_g$; 9(b) shows the coefficient $B_2$ obtained from linear fit $\alpha/\alpha_{0.6Tg}=A+BT/T_g$ in thermal region (ii) 0.67-1.0 $T_g$ as a function of glycerol concentration;

FIG. 10 illustrates an apparatus embodying the invention, for measuring absorption of EM radiation;

FIG. 11 illustrates a second apparatus embodying the invention, for measuring intensity of scattered EM radiation;

FIG. 12 shows plots of infrared absorption spectra for sorbitol obtained in the temperature range 113-313 K; and FIG. 13 shows plots derived from the data of FIG. 12, plotting Voigt function fitting parameters for (a) peak central frequency, (b) peak width, (c) peak height and (d) peak area, as a function of reduced (normalised) temperature $T/T_g$.

To exemplify the efficacy of the invention, the inventors characterised two representative glass-forming drugs: acetaminophen (paracetamol) and indomethacin. These amorphous materials differ greatly in their stability. The glass (amorphous phase) of paracetamol has poor stability, while the glass of indomethacin has very good stability, as is known from direct measurements of the crystallisation of these materials during storage.

Figure 1:
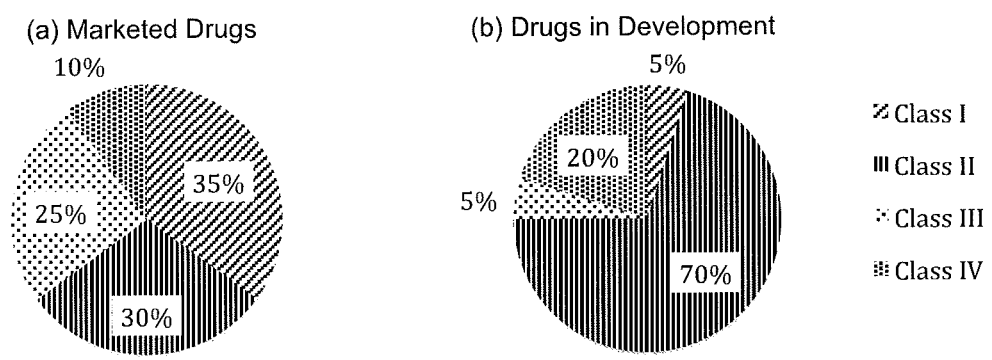
FIG. 1 shows two pie charts illustrating proportions of pharmaceuticals and candidate pharmaceuticals of different BCS Classes.
Figure 2:
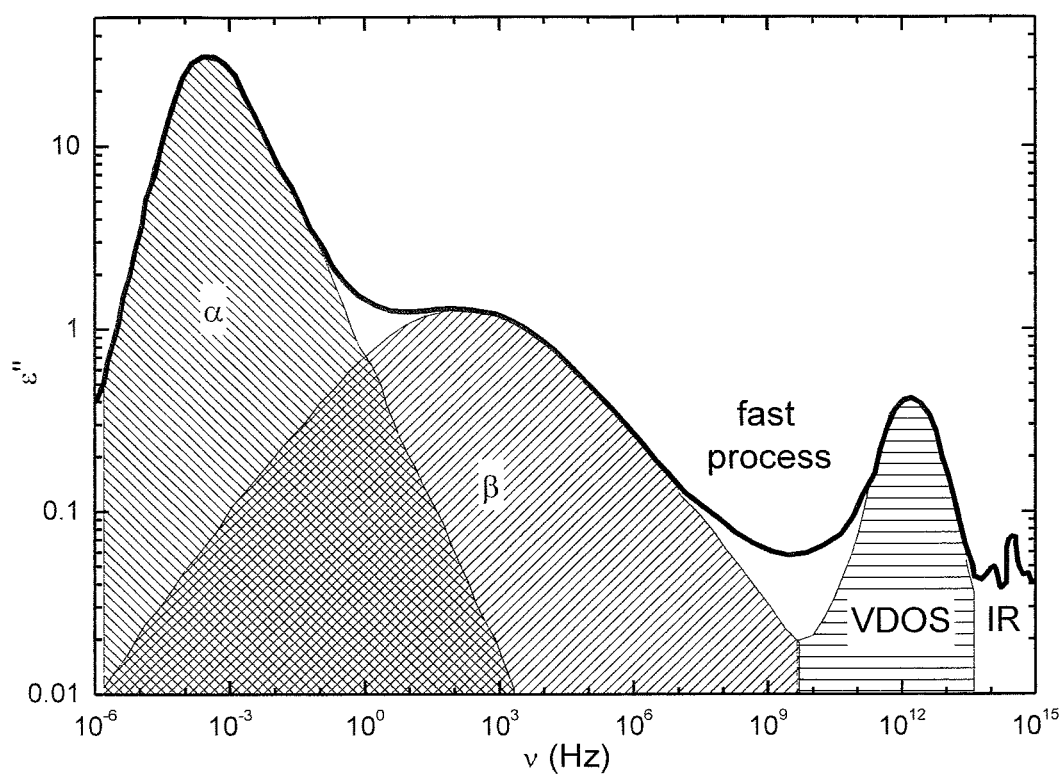
FIG. 2 is a schematic diagram illustrating different molecular mechanisms leading to absorption or scattering of electromagnetic (EM) radiation, in a very broad frequency range. The plot is a generalised case of dielectric losses at some fixed temperatures.
Figure 3:
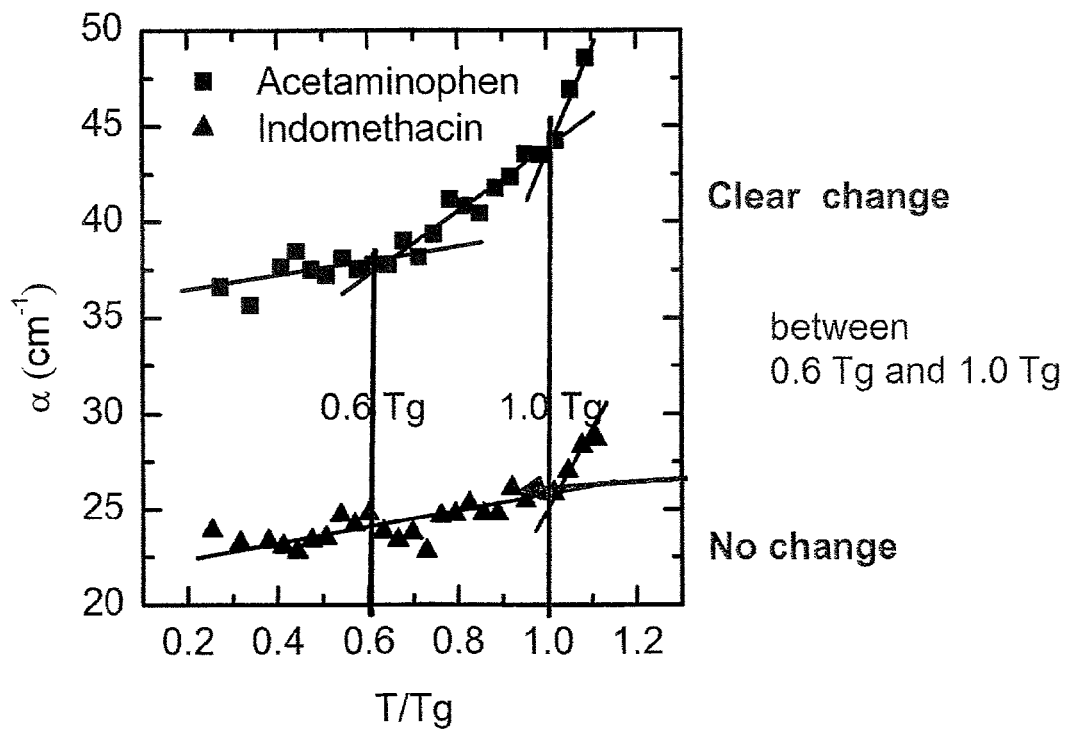
FIG. 3 is a plot of the absorption coefficient for terahertz radiation ($\alpha/cm^{-1}$) measured in transmission through amorphous paracetamol and indomethacin, against normalised temperature (plotted as $T/T_g$)

FIG. 3 plots the results of the characterisation of these materials. FIG. 3 plots the absorption coefficient for terahertz radiation ($\alpha/cm^{-1}$) measured in transmission through the material at 1 THz, against temperature (plotted as $T/T_g$) for each material. As set out in the Summary of the Invention, the rate of change of the loss of EM radiation with temperature (the gradient of the graph in FIG. 3) may then be assessed, or measured, and as appropriate compared with a predetermined value in order to achieve a quantitative, or relative, characterisation of the stability of the amorphous material as described below.

In FIG. 3, the plotted results for indomethacin show two distinct linear regions, firstly a small and constant rate of change, or gradient, for the absorption of the radiation below $T_g$, and secondly a marked change to a higher rate of change, or gradient, above $T_g$. By contrast the plotted results for paracetamol show three different linear regions, namely a low rate of change below a transition temperature of about 0.6 $T_g$, a higher rate of change between 0.6 $T_g$ and $T_g$, and a still higher rate of change above $T_g$.

In other words, FIG. 3 shows that the thermal change in absorption of terahertz radiation between 0.6 $T_g$-1.0 $T_g$ is well developed in paracetamol but very low in indomethacin.

The implication of this is that below $T_g$, the structure of the amorphous phase of indomethacin shows little or no freedom for any molecular movement, whereas the greater absorption of terahertz radiation by amorphous paracetamol between 0.6 $T_g$ and $T_g$ indicates a much greater freedom for molecular movement below $T_g$. This correlates with, and predicts, the resistance to crystallisation of these amorphous materials at temperatures below $T_g$. Amorphous paracetamol crystallises rather readily below $T_g$, whereas amorphous indomethacin is much more stable if stored below $T_g$.

These results can be quantified by comparing the rates of change, or gradients, of the linear sections of the measured data in FIG. 3 with appropriate predetermined values such as threshold values. For example, if a developer of an amorphous pharmaceutical product wishes to characterise the stability of amorphous paracetamol and indomethacin as being above or below a predetermined or desired threshold level of stability, then the gradients of the linear sections of the plots in FIG. 3 may be compared with threshold gradient levels (determined in accordance with the level of stability required), and the stability of paracetamol, indomethacin and any other desired pharmaceuticals compared with the desired threshold value(s). This may either be assessed in terms of whether or not a particular amorphous material falls above or below a predetermined threshold, or more quantitatively in terms of how far above or below the threshold the material falls. The gradients of the data in each of the regions in FIG. 3 may be assessed with reference to predetermined values, but to predict the stability of amorphous materials below $T_g$, it is believed that the gradient in the region 0.6 $T_g$ to $T_g$ is the most critical.

In addition to the consideration of the gradients, the changes of gradient for the data for each material may be assessed and compared with predetermined values. For example, the negligible change in gradient at the transition temperature (0.6 $T_g$) for indomethacin indicates that very little molecular mobility develops as the temperature rises towards $T_g$, whereas the much greater change in gradient for paracetamol at the transition temperature indicates that significant molecular mobility develops as the temperature rises towards $T_g$. The changes in gradient may be measured and compared with a predetermined, or desired, threshold value of the change in gradient corresponding to a desired level of stability of the amorphous material. A quantitative assessment may be made with reference to how far above or below the threshold the measured value falls.

In further embodiments or examples of the invention, a series of polyhydric alcohols were studied. These examples show, using terahertz time-domain spectroscopy (THz-TDS), dielectric losses in the frequency range 0.2-3 THz and the temperature range 80-310 K (straddling the glass-transition temperature), for a series of inter-molecular hydrogen-bonded polyalcohols, $C_n(OH)_nH_{n+2}$: glycerol (n=3), threitol (n=4), xylitol (n=5) and sorbitol (n=6).

These glass-forming liquids show (as known from earlier investigations) a systematic change in the fragility index, $m=\partial \log \eta/\partial(T_g/T)_{T=T_g}$, i.e. in the degree of the non-Arrhenius temperature dependence of the viscosity, $\eta$, m=57 (glycerol), 79 (threitol), 94 (xylitol), 128 (sorbitol), indicative of a decreasing extent of a hydrogen-bonded network. Moreover, these materials show significant differences in their dielectric spectra. They can be ordered in terms of the observation of Johari-Goldstein $\beta$ (JG-$\beta$) relaxation, from a wing-type scenario to a fully resolved JG-$\beta$ relaxation peak, in the series glycerol, threitol, xylitol and sorbitol. Both well below and above $T_g$, only limited experimental dielectric-loss spectra are available at near-terahertz frequencies in the literature for these and other glass-formers obtained by conventional methods. The inventors' THz-TDS data, using embodiments of the invention, show a universal response amongst the studied polyalcohol samples for the microscopic peak at terahertz frequencies, and the first observation of the JG-β relaxation vanishing from terahertz spectra universally at the temperature 0.6$T_g$.

In these examples, systematic THz-TDS study allows direct access to the complex dielectric function for the frequency range of 0.1-3 THz, over a wide range of temperatures. For these experiments, the samples were melted (except glycerol, which is liquid at room temperature), loaded into a continuous-flow cryostat and cooled at a rate of approximately 25 K·min$^{-1}$ to 80 K, followed by subsequent heating by 10 K increments to 310 K. Spectra were acquired using a THz-TDS setup operating in transmission geometry. All four polyalcohols were purchased from Sigma-Aldrich with >99% purity. The samples were used without further purification.

FIG. 4 shows the measured dielectric losses $\in"(v)$ of: (a) glycerol; (b) threitol; (c) xylitol; and (d) sorbitol, at terahertz frequencies in the temperature range 80-310 K measured at 10 K temperature increments. The filled and empty circles highlight the losses in the proximity of 0.6$T_g$ and $T_g$, respectively. The sample of threitol recrystallised above 250 K and only data below this temperature are shown in this figure.

FIG. 5 shows the dielectric losses $\in"(T/T_g)$ at four different frequencies for sorbitol. The solid lines represent linear fits to the data in regions (i) below a transition temperature of about 0.6 $T_g$, (ii) between the transition temperature and $T_g$, and (iii), above $T_g$. The dashed vertical lines highlight the temperatures 0.6$T_g$ and $T_g$, respectively. $T_β$ and $T_α$ represent the crossover points (changes in gradient) of the linear fits from region (i) to region (ii), and from region (ii) to region (iii), respectively. As described for paracetamol above, the data for sorbitol shows three distinct rates of change, or gradients, in regions (i), (ii) and (iii). The relatively high gradient in region (ii) and the distinct changes in gradient at the crossovers between the regions indicate relatively poor stability in amorphous sorbitol. The inventors found that the highest signal-to-noise ratio was provided by the data at 1 THz.

FIG. 6 shows the dielectric losses $\in"(T/T_g)$ at a frequency v=1 THz for all four of the polyalcohols. The solid lines represent linear fits to the data in regions (i), (ii) and (iii), as explained above. The dashed vertical lines highlight the temperatures 0.6$T_g$ and $T_g$, respectively. $T_β$ and $T_α$ represent the crossover points of the linear fits from region (i) to region (ii), and from region (ii) to region (iii), respectively. The dielectric-loss data for sorbitol and glycerol are offset vertically in the positive and negative directions by 0.1, respectively, for clarity.

Three common features were observed in the dielectric losses, $\in"$, of the series of polyhydric alcohols: at temperatures well below the glass transition, $\in"(v)$ comprises a temperature-independent microscopic peak, which persists also into the liquid phase, and which the inventors identify as being due to librational/torsional modes. For 0.6 $T_g$<T<$T_g$, additional thermally-dependent contributions are observed and the inventors found strong evidence for its relation to the Johari-Goldstein secondary β-relaxation process. Clear spectroscopic evidence is found for a secondary β glass transition at 0.6$T_g$. At temperatures above $T_g$, the losses become dominated by primary α-relaxation processes.

The temperature dependence of $\in"(v)$ at v=1 THz is shown in FIG. 6 for all four polyalcohol materials. Here, we use the rescaled temperature T/$T_g$ on the abscissa to compare the common features of the glassy state between the different polyalcohols. Three absorption regimes can be resolved in all samples: (i) temperature-independent losses; ii) a weak temperature dependence of losses below $T_g$; and iii) a strong temperature dependence of losses above $T_g$, as proposed previously. More detailed information was extracted by fitting the data points with an empirical linear fit, viz. $\in"(T/T_g)=A+BT/T_g$, in each of the respective temperature regions. In Table I, we summarize the crossover temperatures $T_β$ and $T_α$ between regions (i)-(ii) and (ii)-(iii), respectively, together with the respective gradients $B_{1,2,3}$ obtained separately for each region, (i), (ii) and (iii). For all samples, Tα corresponds to $T_g$, the temperature above which the temperature-dependent part of $\in"(v)$ becomes dominated by the primary dielectric relaxation.

TABLE 1

Glass-transition temperature, $T_g$, together with parameters for the empirical linear temperature-dependent behavior used to analyse the dielectric losses, ε" (T/$T_g$) = A + BT/$T_g$, as shown in FIG. 6. n stands for the number of OH groups per molecule. $T_β$ and $T_α$ represent the crossover points of the linear fits from region (i) to region (ii), and from region (ii) to region (iii), respectively. B1, 2, 3 are the linear coefficients obtained from fits in regions (i), (ii) and (iii), respectively. The numbers in the brackets state the standard deviation at the last decimal place.

| Sample | n | $T_g$ [K] | $T_α$ [K] | $T_β$ [K] | $T_β/T_g$ | $B_1$ | $B_2$ | $B_3$ |
|---|---|---|---|---|---|---|---|---|
| sorbitol | 6 | 268.3 | 265 | 150 | 0.56 | 0.02(2) | 0.34(2) | 1.92(5) |
| xylitol | 5 | 247.8 | 248 | 167 | 0.68 | 0.06(1) | 0.13(3) | 0.82(4) |
| threitol | 4 | 226.3 | 228 | 147 | 0.65 | 0.07(1) | 0.09(1) | 0.43(15) |
| glycerol | 3 | 191.7 | 189 | — | — | | 0.03(1) | 0.64(1) |

The plotted data in FIG. 6 reveal two striking features. First, they show that the weak temperature dependence of losses (region (ii) in FIG. 6 for threitol, xylitol and sorbitol emerges at a temperature of around 0.6$T_g$ in all cases. Considering that the thermal changes of $\in"$ originate from the secondary relaxation, and most likely from the JG-β relaxation, this means that the secondary relaxation decouples completely from the microscopic peak at around 0.6$T_g$. This observation is in excellent qualitative agreement with calorimetric studies of glass-forming liquids, where the β-glass-transition temperature has been linked to spontaneous temperature drift rates in the region of 0.5-0.7$T_g$. A correlation has been proposed between the fragility index m and a "correlation index" c, defined as $(1-c)=T_{gβ}/T_{gα}$. From the examples of the invention, it is apparent, however, that such a correlation does not hold since these polyalcohols cover a range of different fragilities yet, in all cases, the onset of secondary relaxation is observed in the range of 0.5-0.7 $T_g$.

A striking observation in the THz data is that the temperature gradient, $B_2$, of the dielectric losses in region (ii) varies significantly between the samples (see Table I). Based on the value of $B_2$, the polyalcohols can be arranged in the series, glycerol, threitol, xylitol to sorbitol, i.e. in increasing order of fragility, in analogy with how well the JG-β relaxation peak is resolved from the primary relaxation in the dielectric spectrum at lower frequencies, from an excess wing in glycerol to the strong JG-β peak in sorbitol. A previous study revealed that the number of —OH groups in polyhydric alcohols plays an essential role in the slow dynamics of these materials. This hints that the H-bonding character of molecules in these glasses plays a similar role in both primary and secondary relaxation. One of the implications is that the observations presented here may be characteristic of hydrogen-bonded systems.

To characterise these amorphous materials, values of the gradients, and of gradient $B_2$ in region (ii) in particular, may be compared with predetermined values corresponding to desired levels of amorphous material stability. For example, if it has been determined, for example by experiment, that a threshold value of $B_2$ of 0.1 is acceptable for amorphous materials for a desired application, then according to the data in Table 1, threitol and glycerol exhibit stability above the threshold (i.e. a lower value of gradient $B_2$). Alternatively, or in addition, the changes in gradient between regions (i) and (ii), i.e. $B_2-B_1$, may be compared with predetermined values corresponding to desired levels of amorphous material stability. In other words, the value $B_1$ may effectively be used as the predetermined threshold value to which the value $B_2$ (for the same material) may be compared. In general, the lower the value of $B_2-B_1$, or the closer the value of $B_2-B_1$ is to zero, the more stable the amorphous phase of the material.

Predetermined threshold values may also, or in addition, be determined by experiment, for example by measuring corresponding values for amorphous materials known (for example from tests of stability against crystallisation at predetermined usage or storage temperatures, or from accelerated tests at elevated temperatures) to have acceptable and unacceptable stability for a desired application of the materials.

The quantitative difference between a measured value and a predetermined value may additionally indicate quantitatively the stability of an amorphous material above or below a threshold level.

In conclusion, using terahertz time-domain spectroscopy, the inventors have studied dielectric losses in the supercooled hydrogen-bonded polyalcohols, glycerol, threitol, xylitol and sorbitol, at terahertz frequencies, at temperatures both above and below $T_g$. The results reveal several universal features amongst the samples. At the lowest temperatures, the losses comprise the microscopic peak due to librational/torsional modes. As the glasses are heated above a transition temperature of about $0.67T_g$, the dielectric losses increase steadily with temperature. There is strong evidence that this feature originates from the high-frequency tail of the JG-$\beta$ relaxation. It is best observed in the case of sorbitol, while it remains unobservable in the case of glycerol. Temperatures in the proximity of $0.67T_g$ appear to be the universal region for the secondary glass transition in several systems, but with no correlation to the fragility, as has been proposed previously. When the glasses are heated above $T_g$, the dielectric losses become dominated by the high-frequency tail of the $\alpha$-relaxation that shifts to higher frequencies. This observation offers a microscopic interpretation of $T_g$ as being the temperature where the primary dielectric relaxation decouples from the libration-vibration band. The temperature variation of the losses, both above and below $T_g$, that originate from relaxation processes increases with the number of —OH groups per molecule. This finding highlights the possibility that the character of inter-molecular bonding plays an important role in both primary and secondary relaxations.

A further embodiment, illustrated with reference to FIGS. 7 and 8, considers calibration for estimation of drug stability against crystallisation. Here the inventors show an example of calibration of stability of amorphous drug system based on the terahertz absorption coefficient. The drug system is naproxen/indomethacin mixture with molar fractions NAP:IND=1:2 and 1:1. The NAP:IND 1:2 mixture started to recrystallise within 21 days when stored at room temperature (298 K), while the NAP:IND 1:1 mixture remained amorphous for 35 days.

There is an absolute difference in the absorption coefficient, $\alpha$, and glass transition temperature, $T_g$, between the two molar fractions originating from their different composition (FIG. 7). In order to compare the two samples the inventors therefore calculated a relative absorption coefficient, $\alpha/\alpha_{0.6T_g}$ measuring the absorption level $\alpha(T)$ against the absorption at $T=0.6T_g$, $\alpha_{0.6T_g}$ (i.e. at the onset of the sub-$T_g$ mobility responsible for the crystallisation, FIG. 8). The rescaled absorption coefficient shows a linear change with rescaled temperature $T/T_g$ and can be fitted by a linear function $\alpha/\alpha_{0.6T_g} C+DT/T_g$. Here the parameter D describes the increase in the absorption, which reflects on the level of sub-$T_g$ molecular mobility. The parameter $D_1$ describes the absorption below $0.67T_g$, which may also originate from secondary relaxations that are however not thought of being responsible for the crystallisation of amorphous drugs. The parameter $D_2$ describes the absorption above $0.6T_g$ that is thought to originate from the same processes as $D_1$ with extra contribution of the secondary relaxations related to the sample crystallisation. The change of the relative absorption above and below $T=0.6T_g$, i.e. $D_2-D_1$, correlates to the stability of the amorphous phase: the lower the value of $D_2-D_1$, the longer the drug is expected to stay amorphous. For this particular case of the NAP:IND system outlined above the sample with $D_2-D_1<0.18$ showed greater stability than the system with a $D_2-D_1>0.94$. A calibration for multiple mixtures or formulations can be made using this method (Table 2).

TABLE 2

Calibration of the sub-$T_g$ terahertz losses in naproxen/indomethacin mixture system with molar fractions NAP:IND = 1:2 and 1:1. The relative level of the sub-$T_g$ losses is expressed in coefficient $D_2 - D_1$, obtained from fit $\alpha/\alpha_{0.6\ T_g} = C + DT/T_g$ in the thermal regions between 0.2-0.6 $T_g$ (index 1) and 0.6-1.0 $T_g$ (index 2).

| Sample | $T_g$ [K] | $\alpha_{0.6\ T_g}$ [cm$^{-1}$] | $D_1$ | $D_2$ | $D_2 - D_1$ | Stability at 298 K. |
|---|---|---|---|---|---|---|
| NAP IND 12 | 305.16 | 18.0 | 0.25(3) | 1.19(3) | 0.94(4) | <21 days |
| NAP IND 11 | 298.45 | 18.5 | 0.08(3) | 0.26(5) | 0.18(6) | <35 days |

A further embodiment of the invention illustrates its use in the optimization of glassy matrix formulation for protein stabilisation.

Sugars may be usable for protecting dried biological structures, such as lipid membranes or proteins, even under complete desiccation, creating a suspended state of biological activity in the dry state that can be recovered almost miraculously upon hydration. This embodiment shows an example of optimization of glassy matrix formulation for protein stabilisation, using a mixture of trehalose and glycerol. Trehalose and glycerol glasses have been studied by incoherent neutron scattering and it was found that glycerol might make the trehalose glass more rigid on the inter-molecular level, despite its plasticising effect. In particular, these experiments have suggested that a 2.5% glycerol/97.5% trehalose mass ratio is the most rigid.

In the embodiment, trehalose di-hydrate and glycerol were sourced from Sigma-Aldrich. UK, and used as received. Three samples were studied: pure trehalose, 2.5% glycerol/97.5% trehalose and 5% glycerol/95% trehalose (weight fraction). The glass transition temperatures of different samples are summarized in Table 3.

TABLE 3

Glass transition temperature for trehalose/glycerol mixtures

| | Glycerol weight concentration | | | |
|---|---|---|---|---|
| | 0% | 2.5% | 5% | 100% |
| $T_g$ [K] | 388 | 379 | 370 | 190 |

Trehalose di-hydrate crystalline powder was first mixed with glycerol and then melted ($T_m \approx 480$ K). Particular care was given to take into account mass change of trehalose after losing water and becoming anhydrous during heating. The liquid melts were loaded in a cryostat sample cell, cooled to room temperature, attached to a cryostat and then cooled down to 80 K before the start of the measurement. The samples were then heated with 20 K step increments between 80-480 K. At each temperature step, reference and sample spectra were acquired.

The experimental results show that there is an absolute difference in the absorption coefficient, a, and glass transition temperature, $T_g$, between the different molar fractions originating from their different composition. In order to compare the samples the inventors therefore calculated a relative absorption coefficient, $\alpha/\alpha_{0.6Tg}$, measuring the absorption level $\alpha(T)$ against the absorption at $\alpha_{0.6Tg} = \alpha(0.6T_g)$ (i.e. at the onset of the sub-$T_g$ mobility responsible for the crystallisation). The dependence of $\alpha/\alpha_{0.6Tg}$ on reduced temperature $T/T_g$ is shown in FIG. 9(a).

The data in FIG. 9(a) are split into three thermal regions: (i) below 0.67 $T_g$, (ii) 0.67-1.0 $T_g$ and (iii) above 1.0 $T_g$. Each region can be fitted by a linear function $\alpha/\alpha_{0.6Tg} = A + BT/T_g$. Here the parameter B describes the increase in the absorption, which reflects on the level of molecular mobility. In particular, coefficient $B_2$ from the linear fit in the region (ii) can be associated with secondary relaxations that are strongly correlated to the stability (rigidity) of the glass at temperatures below $T_g$. The parameter $B_2$ obtained for different mixtures is shown in FIG. 9(b) as a function of glycerol concentration.

From FIG. 9(b) it is clear that $B_2$ is lowest at 2.5% glycerol concentration. This means that the trehalose/glycerol glass has lowest inter-molecular mobility at this concentration. In other words, the glass is most rigid in this case, which is well in line with previous observations by neutron scattering mentioned above.

A further embodiment, with reference to FIGS. 12 and 13, illustrates the use of FTIR to characterise or evaluate the interaction of the amorphous material in a desired energy range.

FIG. 12 plots FTIR spectra for sorbitol, in a temperature range between 113 K and 313 K, at a range of infrared (IR) frequencies between about 72 THz and 100 THz (wavenumbers 2400 cm$^{-1}$ to 3600 cm$^{-1}$). The vertical axis of the plot represents infrared absorbance, in arbitrary units. In this IR frequency range, it is understood that IR absorbance occurs due to stretching of C—H bonds and O—H bonds in the sorbitol. As described above, however, where the —H and —OH species are hydrogen bonded to other molecules in the sorbitol, the stretching of the C—H bonds and, in particular, of the O—H bonds will be affected. This may affect the fundamental vibrational modes of the bonds and/or overtones thereof. Measurement of the IR absorbance using FTIR therefore allows characterisation of the hydrogen bonds involved in intermolecular bonding, which have an energy falling within the terahertz energy range (e.g. $6.6 \times 10^{-24}$ J to $6.6 \times 10^{-21}$ J) involved in embodiments of the present invention, even though the energy of the IR radiation itself falls outside this range.

In general, as illustrated by this embodiment, the inventors expect O—H bonds to be more strongly affected by inter-molecular hydrogen bonding than N—H or C—H bonds, and so the measurement of O—H bonds by techniques such as FTIR may provide the best characterisation of the hydrogen bonds. But measurement of N—H and C—H and other bonds may also be effective.

FIG. 13 shows four plots derived (by curve fitting, or function fitting) from the measured data in FIG. 12 for the absorbance peak corresponding to the O—H bonds in the sorbitol.

In FIG. 13(a), the frequency (wavenumber) of the FTIR absorbance peak measured at each temperature is plotted against reduced temperature, $T/T_g$. In FIG. 13(b), the widths of the FTIR absorbance peaks are plotted against reduced temperature. In FIG. 13(c), the heights of the FTIR absorbance peaks are plotted against reduced temperature. And in FIG. 13(d), the areas beneath the FTIR absorbance peaks are plotted against reduced temperature.

It is striking that the data in all four of the plots in FIG. 13 show three linear portions, of different gradients, corresponding to the temperature ranges below 0.67 $T_g$, between 0.67 $T_g$ and $T_g$, and above $T_g$, with kinks or corners in the plots at 0.67 $T_g$ and $T_g$ This is the same as was seen in the terahertz radiation adsorption data for sorbitol shown in FIGS. 5 and 6 and discussed above and demonstrates that the FTIR technique is responsive to the same interaction of the amorphous material (the sorbitol) as the terahertz adsorption technique. The FTIR technique therefore provides an alternative way to characterize or evaluate the desired interaction of the amorphous material, in the terahertz energy range, embodying the invention.

In the same way as described above for the terahertz spectroscopy method, FTIR data may therefore be used to evaluate the stability of amorphous materials, and data derived from FTIR may be compared with predetermined threshold values of gradient, or used to compare the relative stability of one material compared to another.

FIG. 10 illustrates an apparatus embodying the present invention. The apparatus comprises a transmission terahertz spectrometer. It starts with a laser system 2 comprising a continuous wave pump laser and a Ti:Sapphire oscillator producing femtosecond pulses at central wavelength 800 nm. A beam splitter splits the laser beam into terahertz-generating and terahertz-sensing parts 4, 6.

The terahertz-generating part comprises a photoconductive emitter 8. The emitter is made from a semiconductor substrate (GaAs) and has two electrodes of bow-tie structure separated by a narrow gap of a few hundred microns. The laser beam generates conducting charge carriers (electrons and holes) in the semiconductor that are accelerated by a voltage applied to the electrodes of the emitter, resulting in a photocurrent. The decay of the photocurrent produces terahertz radiation that is collected and focused by parabolic mirrors 10, 12 onto a sample plane.

A sample of amorphous material 14 sits in the sample plane in a compartment that allows transmission of terahertz radiation. This is commonly a sandwich structure of two terahertz-transparent windows, transparent at terahertz frequencies, separated by a spacer with a central aperture. The aperture is filled with the sample and the sandwich structure is attached to a cold finger of a cryostat that allows the sample to be controllably cooled/heated. Terahertz radiation penetrates the sandwich structure and is collected and focused by further parabolic mirrors 16, 18 onto a ZnTe crystal 20.

The sensing part 6 of the femtosecond beam is led from the beam splitter through an optical delay stage 22 to the ZnTe crystal 20. The terahertz field creates the Pocket's effect in the ZnTe crystal that changes the polarisation of the sampling femtosecond beam. The change in the polarization of the optical beam is analyzed by a quarter-wave plate 24, an analyser (Wollaston prism) 26 and two balanced photodiodes 28. The quarter-wave plate is used to balance the signal on the photodiodes when no THz field is present in the ZnTe. The analyser is used spatially to separate two orthogonal polarizations of the femtosecond beam, which are detected by the balanced photodiodes. The difference signal from the photodiodes is then collected and processed electronically by a processor 30. The terahertz part of the setup sits in a box 32 that can be operated under vacuum or dry nitrogen atmosphere to eliminate absorption of terahertz radiation by water vapour.

In this apparatus, a photoconductive antenna is used for terahertz radiation emission and an optoelectronics approach is used for detection. Other apparatus embodying the invention may differ in the terahertz generation (e.g. different antenna type, usage of quantum cascade lasers, photomixing, or any other suitable system), terahertz detection (e.g. using photoconductive antenna, GaP crystal, bolometer or any other suitable system) as well as in the way the terahertz beam is transmitted through the sample (e.g. using elliptical mirrors instead of parabolic, using a different sample compartment, or changing the geometry from transmission to reflection mode, where reflected terahertz beam is collected).

The processor 30 is advantageously suitably programmed to control the apparatus to generate the results required in embodiments of the invention, for example to measure the absorption of radiation by the sample at a range of temperatures, to evaluate the rate of change of absorption with temperature and/or any discontinuity in the rate of change of absorption with temperature at a transition temperature, so that these measured parameters can be compared with predetermined values, or thresholds.

FIG. 11 illustrates a further apparatus embodying the present invention. This apparatus is for measuring interactions between an amorphous material and EM radiation in the form of EM radiation scattered from a sample of the amorphous material.

A sample of an amorphous material 56 is held in a cryostat to control its temperature. A laser 51 generates a beam of EM radiation which is guided and focused by mirrors 52, filters 53, a filter/beam splitter 54 and focussing optics 55 onto the sample. The frequency of the EM radiation is such as to cause scattered radiation due to an energy change or transition in the amorphous material corresponding to the energy of a frequency of EM radiation between 10 GHz and 10 THz. Neither the laser radiation nor the scattered radiation needs to be of a frequency in the range 10 GHz to 10 THz (though either or both of them may have such a frequency), as long as measurement of the intensity of the scattered radiation provides a measure of a transition in the amorphous material having an energy corresponding to a desired frequency in the range 10 GHz to 10 THz, or other preferred range described herein.

The scattered radiation from the sample is focussed by the focussing optics 55 and passes back through the beam splitter 54, notch filters 57 and further focussing optics 58 before entering a spectrometer 59, where the intensity of the scattered radiation is measured.

Possible Molecular Mechanisms

The following text discusses potential mechanisms giving rise to the experimental results observed in the Examples of the invention. These possible mechanisms do not limit the scope of the claimed invention but illustrate the experimental data by showing the inventors' current thinking behind the invention.

In all four polyalcohol samples, the dielectric losses of the materials in the glassy state at the lowest temperatures are almost independent of temperature and comprise a microscopic peak at a frequency around 2-3 THz, as seen in FIG. 4. The peak is still evident for $T>T_g$, but the amplitude now increases with increasing temperature. The inventors assert that the microscopic peak observed in the THz-TDS data in FIG. 4 is a manifestation of a peak in the vibrational density of states (VDOS) due to low-lying, optically-active librational/torsional modes.

Calculations of the internal vibrational modes in the isolated glycerol molecule show that the lowest (torsional) mode occurs at 2.01 THz. Moreover, lattice-dynamics calculations of phonons in crystalline glycerol, used to generate the orientationally averaged (powder) 'glass-like' dynamical structure factor in the incoherent approximation, indicate a peak at ~1.5 THz. The lowest-frequency optical modes in crystalline glycerol are observed from RS to occur at 1.65 THz. These findings support our assertion that the microscopic peak in FIG. 4 is due to low-frequency librational/torsional modes in these materials.

The temperature-dependent contributions to the dielectric losses below $T_g$ are most pronounced in the case of sorbitol. In order to elucidate what leads to these additional losses, we subtracted the contribution of the microscopic peak from the dielectric-loss spectra, as $\epsilon''(v)-\epsilon''_{100K}(v)$ (as shown in FIG. 5). It is immediately clear that, above $T_g$ (shown as circles in FIG. 5), the dielectric losses resemble the tail of a broad peak with a maximum at frequencies below 1 THz, which links the origin of this loss to the primary dielectric-relaxation process commonly observed by dielectric spectroscopy. At $T_g$, the primary dielectric relaxation corresponds to relaxation times of around 100 seconds, or characteristic frequencies of ~$10^{-2}$ Hz, far too low to contribute to $\epsilon''(v)$ in the terahertz regime. Upon heating above $T_g$, the primary relaxation rapidly shifts to higher frequencies, resulting in the observed increase in dielectric losses. This gives the glass transition a new physical meaning. Very often, $T_g$ is addressed on a macroscopic level as the temperature corresponding to a given arbitrary value of the viscosity (e.g. $10^{12}$ Pa s) in the middle of the thermal region where the viscosity increases by many orders of magnitude, or as the temperature in the middle of a step in the enthalpy, as observed by DSC. From the results presented here, it is possible to address $T_g$ on a microscopic level as the temperature where the primary dielectric relaxation decouples from the temperature-independent microscopic peak and no longer contributes to the losses at THz frequencies.

In the case of sorbitol, the changes in dielectric losses below $T_g$ are observed only down to 170 K. At lower temperatures, the losses are substantially constant. The change in losses with temperature below $T_g$ are roughly one order-of-magnitude weaker compared to the contribution of the α-relaxation to the dielectric losses above $T_g$ This suggests that the source of the losses below $T_g$ no longer originates from the α-relaxation process. The contribution of the losses below $T_g$ is not uniform across the spectrum but slightly higher losses are detected at lower frequencies, which we attribute to the high-frequency tail of a process, such as the secondary relaxation, shifting to lower frequencies with decreasing temperature. Indeed, a change in $\in''$ of the order of $10^{-2}$ with a 10 K increment was observed at GHz frequencies in dielectric spectra of sorbitol below $T_g$, and can be assigned to the JG-$\beta$ relaxation.

A different possible molecular mechanism lies is the so-called fast-secondary relaxation. This type of relaxation is often explained as a rattling of a molecule in a cage of neighbouring molecules. The process is usually observed in GHz-THz frequency range, or ns-ps time scale, and there is a growing evidence that this fast movements play a role in the supercooled liquids above Tg. The fast-secondary relaxation process has been also shown to be important in the stabilisation of proteins in glassy matrices.

In a first aspect, there is provided a method for characterising an amorphous material, comprising the steps of: evaluating a rate of change of an interaction of the amorphous material with electromagnetic (EM) radiation with temperature, at an energy corresponding to EM radiation of frequency between 10 GHz and 10 THz, in a temperature range below a glass transition temperature. $T_g$; and comparing the rate of change with a predetermined value.

The energy of the interaction may be between $6.6 \times 10^{-24}$ J and $6.6 \times 10^{-21}$ J.

The rate of change may be evaluated within a temperature range between $T_g$ and a lower temperature.

The lower temperature may be between 0.4 and 0.8 $T_g$, preferably between 0.5 and 0.7 $T_g$, or between 0.55 and 0.05 $T_g$, and is particularly preferably 0.6 $T_g$.

The method according to the first aspect may comprise the steps of; evaluating a first value of the rate of change in a temperature range between $T_g$ and a transition temperature below $T_g$; evaluating a second value of the rate of change in a temperature range below the transition temperature; and using the second value of the rate of change as the predetermined value for comparison with the first rate of change.

The transition temperature may be between 0.4 and 0.8 $T_g$, preferably between 0.5 and 0.7 $T_g$ or between 0.55 and 0.65 $T_g$, and is particularly preferably 0.6 $T_g$.

The interaction may be evaluated for an EM frequency or frequencies between 100 GHz and 3 THz, between 0.5 THz and 2 THz, preferably between 0.75 THz and 1.5 THz, and particularly preferably at 1 THz.

The interaction may be measured at a plurality of frequencies within a range of frequencies, and the rate of change of the interaction with temperature is evaluated at the EM frequency within that range of frequencies which provides the interaction data with the highest signal-to-noise ratio.

The interaction may be measured and the rate of change of the interaction may be evaluated using EM radiation at a frequency or frequencies between 100 GHz and 3 THz, between 0.5 THz and 2 THz, preferably between 0.75 THz and 1.5 THz, and particularly preferably at 1 THz.

The evaluation of the rate of change of the interaction of the amorphous material with EM radiation may comprise the evaluation of the rate of change of loss of EM radiation of frequency between 10 GHz and 10 THz on passing through the amorphous material.

The loss of EM radiation may be expressed in terms of an absorption coefficient of the amorphous material, a dielectric loss value for the amorphous material, an extinction coefficient for the amorphous material, an amplitude of transmittance, an amplitude of reflectance, an amplitude of time-domain peak, or absorbance, or any combination of these.

The evaluation of the rate of change of the interaction of the amorphous material with EM radiation may comprise the evaluation of the rate of change of an intensity of scattered EM radiation at a frequency or frequency shift of between 10 GHz and 10 THz.

The scattered radiation may derive from EM radiation interacting with the amorphous material.

The scattered radiation derives from Raman, VIS light or neutron spectroscopy or scattering.

The evaluation of the rate of change of the interaction of the amorphous material with EM radiation comprises the evaluation of the rate of change of an intensity of frequency-shifted EM radiation at a frequency or a frequency shift of between 10 GHz and 10 THz.

The frequency-shifted radiation may be due to fluorescence, for example as measured using a time-resolved fluorescence spectroscopy technique, such as time-resolved fluorescent Stokes shift spectroscopy.

The evaluation of the rate of change of the interaction of the amorphous material may comprise FTIR spectroscopy, IR spectroscopy, near-IR spectroscopy or NMR spectroscopy.

The amorphous material may comprise a hydrogen-bonded amorphous material.

The amorphous material may comprises a pharmaceutically-active material or a candidate pharmaceutical material.

The amorphous material may comprise a polymeric material.

The method may comprise the step of using the characterisation of the amorphous material to assess or predict the resistance to crystallisation of the amorphous material.

The method may comprise the step of using the characterisation of the amorphous material to assess or predict the resistance to crystallisation of the amorphous material under predetermined conditions.

The method may comprise the step of using the characterisation of the amorphous material to assess or predict a stabilising effect of the amorphous material.

According to a second aspect there is provided an apparatus for characterising an amorphous material, comprising: a spectrometer for measuring an interaction of the amorphous material with electromagnetic (EM) radiation at an energy corresponding to EM radiation of frequency between 10 GHz and 10 THz; and a processor for evaluating a rate of change of the interaction with temperature, in a temperature range below a glass transition temperature, $T_g$, of the amorphous material, and for comparing the rate of change with a predetermined value.

The energy of the interaction may be between $6.6 \times 10^{-24}$ J and $6.6 \times 10^{-21}$ J.

The rate of change may be evaluated within a temperature range between $T_g$ and a lower temperature.

The lower temperature may be between 0.4 and 0.8 $T_g$, between 0.5 and 0.7 $T_g$, preferably between 0.55 and 0.65 $T_g$, and particularly preferably 0.6 $T_g$.

The apparatus may be for measuring the interaction and evaluating a first value of the rate of change in a temperature range between $T_g$ and a transition temperature below $T_g$, measuring the interaction and evaluating a second value of the rate of change in a temperature range below the transition temperature, and using the second rate of change as the predetermined value for comparison with the first rate of change.

The transition temperature may be between 0.4 and 0.8 $T_g$, between 0.5 and 0.7 $T_g$, preferably between 0.55 and 0.65 $T_g$, and particularly preferably 0.6 $T_g$.

The interaction may be measured for a frequency or frequencies between 100 GHz and 3 THz, between 0.5 THz and 2 THz, preferably between 0.75 THz and 1.5 THz, and particularly preferably at 1 THz.

The interaction may be measured within a range of frequencies of EM radiation, and the rate of change of the interaction with temperature is evaluated at the EM frequency within that range of frequencies providing the interaction data with the highest signal-to-noise ratio.

The interaction may be measured and the rate of change is evaluated using EM radiation of between 100 GHz and 3 THz, between 0.5 THz and 2 THz, preferably between 0.75 THz and 1.5 THz, and particularly preferably at 1 THz.

The measurement of the interaction of the amorphous material with EM radiation may comprise a measurement of a loss of EM radiation of frequency between 10 GHz and 10 THz on passing through the amorphous material.

The measurement of the interaction of the amorphous material with EM radiation may comprise a measurement of an intensity of scattered EM radiation at a frequency or frequency shift of between 10 GHz and 10 THz.

The scattered radiation may derive from EM radiation interacting with the amorphous material.

The measurement of the interaction of the amorphous material with EM radiation may comprise a measurement of an intensity of frequency-shifted EM radiation at a frequency or a frequency shift of between 10 GHz and 10 THz.

The evaluation of the rate of change of the interaction of the amorphous material may comprise FTIR spectroscopy, IR spectroscopy, near-IR spectroscopy or NMR spectroscopy.

The amorphous material may comprise a hydrogen-bonded amorphous material.

The amorphous material may comprise a pharmaceutically-active material or a candidate pharmaceutical material.

The amorphous material may comprise a polymeric material.

According to a third aspect there is provided a method for characterising an amorphous material, comprising the steps of: evaluating first and second values of a rate of change with temperature of an interaction of the amorphous material with electromagnetic (EM) radiation, at an energy corresponding to EM radiation of frequency between 10 GHz and 10 THz, in respective first and second temperature ranges, the first temperature range being between a glass-transition temperature, $T_g$, of the amorphous material and a transition temperature below $T_g$, and the second temperature range being below the transition temperature; and evaluating a difference between the first and second rate of change values.

The transition temperature may be between 0.4 and 0.8 $T_g$, preferably between 0.5 and 0.7 $T_g$, or between 0.55 and 0.65 $T_g$, and is particularly preferably about 0.6 $T_g$.

According to a fourth aspect there is provided an apparatus for characterising an amorphous material, comprising; a spectrometer for measuring an interaction of the amorphous material with electromagnetic (EM) radiation, at an energy corresponding to EM radiation of frequency between 10 GHz and 10 THz; and a processor for evaluating first and second values of a rate of change of the interaction with temperature, in respective first and second temperature ranges, the first temperature range being between a glass-transition temperature, $T_g$, of the amorphous material and a transition temperature below $T_g$, and the second temperature range being below the transition temperature; and evaluating a difference between the first and second rate of change values.

The transition temperature may be between 0.4 and 0.8 $T_g$, preferably between 0.5 and 0.7 $T_g$, or between 0.55 and 0.65 $T_g$, and is particularly preferably about 0.6 $T_g$.

According to a fifth aspect there is provided an amorphous material produced using the characterisation method of the first or third aspect.

According to a sixth aspect there is provided a method for characterising an amorphous material substantially as described herein.

According to a seventh aspect there is provided an apparatus for characterising an amorphous material substantially as described herein.

According to an eighth aspect there is provided an amorphous material substantially as described herein, or characterised substantially as described herein.

The invention claimed is:

1. A method for characterizing an amorphous material, comprising the steps of:
    measuring, with a spectrometer, an interaction of the amorphous material with electromagnetic (EM) radiation;
    evaluating, with a processor, a rate of change of the interaction of the amorphous material with EM radiation with temperature, at an energy corresponding to EM radiation of frequency between 10 GHz and 10 THz, in a temperature range below a glass transition temperature, $T_g$; and
    comparing, with the processor, the rate of change with a predetermined value.

2. A method according to claim 1, in which the rate of change is evaluated within a temperature range between $T_g$ and a lower temperature.

3. A method according to claim 2, in which the lower temperature is between 0.4 and 0.8 $T_g$.

4. A method according to claim 1, comprising the steps of:
    evaluating, with the processor, a first value of the rate of change in a temperature range between $T_g$ and a transition temperature below $T_g$;
    evaluating, with the processor, a second value of the rate of change in a temperature range below the transition temperature; and
    using the second value of the rate of change as the predetermined value for comparison with the first rate of change.

5. A method according to claim 4, in which the transition temperature is between 0.4 and 0.8 $T_g$.

6. A method according to claim 1, in which the interaction is evaluated for an EM frequency or frequencies between 100 GHz and 3 THz, between 0.5 THz and 2 THz.

7. A method according to claim 1, in which the interaction is measured at a plurality of frequencies within a range of frequencies, and the rate of change of the interaction with temperature is evaluated at the EM frequency within that range of frequencies which provides the interaction data with the highest signal-to-noise ratio.

8. A method according to claim 1, in which the interaction is measured and the rate of change of the interaction is evaluated using EM radiation at a frequency of frequencies between 100 GHz and 3 THz, between 0.5 THz and 2 THz.

9. A method according to claim 1, in which the evaluation of the rate of change of the interaction of the amorphous material with EM radiation comprises the evaluation of the rate of change of loss of EM radiation of frequency between 10 GHz and 10 THz on passing through the amorphous material.

10. A method according to claim 1, in which the evaluation of the rate of change of the interaction of the amorphous material with EM radiation comprises the evaluation of the rate of an intensity of scattered EM radiation at a frequency or frequency shift of between 10 GHz and 10 THz.

11. A method according to claim 10, in which the scattered radiation derives from EM radiation interacting with the amorphous material.

12. A method according to claim 10, in which the scattered radiation derives from Raman, VIS light or neutron spectroscopy or scattering.

13. A method according to claim 1, in which the evaluation of the rate of change of the interaction of the amorphous material with EM radiation comprises the evaluation of the rate of change of an intensity of frequency-shifted EM radiation at a frequency or a frequency shift of between 10 GHz and 10 THz.

14. A method according to claim 1, in which the evaluation of the rate of change of the interaction of the amorphous material comprises FTIR spectroscopy, IR spectroscopy, near-IR spectroscopy or NMR spectroscopy.

15. A method according to claim 1, in which the amorphous material comprises a hydrogen-bonded amorphous material.

16. A method according to claim 1, comprising the step of using the characterization of the amorphous material to assess or predict the resistance to crystallization of the amorphous material.

17. A method according to claim 1, comprising the step of using the characterization of the amorphous material to assess or predict the resistance to crystallization of the amorphous material under predetermined conditions.

18. A method according to claim 1, comprising the step of using the characterization of the amorphous material to assess or predict a stabilizing effect of the amorphous material.

19. An apparatus for characterizing an amorphous material, comprising:
　a spectrometer for measuring an interaction of the amorphous material with electromagnetic (EM) radiation at an energy corresponding to EM radiation of frequency between 10 GHz and 10 THz; and
　a processor for evaluating a rate of change of the interaction with temperature, in a temperature range below a glass transition temperature, $T_g$, of the amorphous material, and for comparing the rate of change with a predetermined value.

20. A method for characterizing an amorphous material, comprising the steps of:
　measuring, with a spectrometer, an interaction of the amorphous material with electromagnetic (EM) radiation;
　evaluating, with a processor, first and second values of a rate of change with temperature of the interaction of the amorphous material with EM radiation, at an energy corresponding to EM radiation of frequency between 10 GHz and 10 THz, in respective first and second temperature ranges, the first temperature range being between a glass-transition temperature, $T_g$, of the amorphous material and a transition temperature below $T_g$, and the second temperature range being below the transition temperature; and
　evaluating, with the processor, a difference between the first and second rate of change values.

* * * * *